United States Patent [19]

Bombardelli

[11] Patent Number: 5,314,906

[45] Date of Patent: May 24, 1994

[54] DERIVATIVES OF PHYSOSTIGMINE, THEIR USE AND PHARMACEUTICAL FORMULATIONS CONTAINING THEM

[75] Inventor: Ezio Bombardelli, Milan, Italy

[73] Assignee: Indena S.p.A., Italy

[21] Appl. No.: 2,794

[22] Filed: Jan. 11, 1993

[30] Foreign Application Priority Data

Mar. 16, 1992 [GB] United Kingdom ................ 9205670

[51] Int. Cl.$^5$ .................... C07D 487/00; A61K 31/40
[52] U.S. Cl. .................... 514/411; 548/429; 424/443; 424/449
[58] Field of Search .................... 548/429; 514/411; 424/443, 449

[56] References Cited

U.S. PATENT DOCUMENTS 4,978,673  12/1990  Merone et al. ................ 548/429

Primary Examiner—Joseph Paul Brust
Assistant Examiner—MarySusan H. Gabilan
Attorney, Agent, or Firm—Kirschstein, Ottinger, Israel & Schiffmiller

[57] ABSTRACT

The therapeutic use of new salts of physostigmine in the treatment of syndromes related to changes in cerebral metabolism in the elderly is described. The new salts of physostigmine, which are based on phosphatidic acid, are highly lipophilic and exhibit excellent bioavailability when administered orally, transcutaneously or transepidermally.

11 Claims, No Drawings

DERIVATIVES OF PHYSOSTIGMINE, THEIR USE AND PHARMACEUTICAL FORMULATIONS CONTAINING THEM

BACKGROUND OF THE INVENTION

1. Field of the Invention

The present invention relates to new derivatives of physostigmine, to processes for their production and to novel pharmaceutical compositions and dosage forms containing them. The invention further relates to the therapeutic use of the novel physostigmine derivatives of the invention in the treatment of syndromes related to changes in cerebral metabolism in the elderly.

2. Description of Related Art

Physostigmine (I) is a well-known alkaloid which has been used as a myotic agent since the beginning of this century. The substance has now almost completely been abandoned for its original therapeutic use. However over the last 15 years it has been found that physostigmine's significant anticholinesterase activity makes it particularly valuable in the treatment of Alzheimer's disease and the severe effects of various forms of senile dementia, since it improves the cholinergic deficit found in the brain of affected patients.

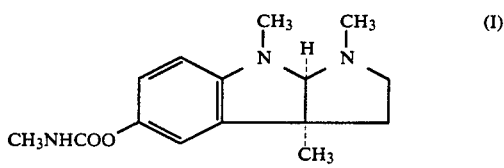

(I)

A number of clinical studies (Davis, Am. J. Psychiat., 139, 1421, 1982; Jotkowitz, Ann. Neurol., 14, 690, 1983; Davis, New Engl. J. Med., 308, 721, 1983) have shown that the intravenous administration of repeated daily doses of physostigmine produced significant improvements in memory. It was also found that when the alkaloid is administered subcutaneously or by mouth, it is degraded rapidly, with the result that treatment must be repeated at short intervals. A further disadvantage of both the intravenous and subcutaneous routes of administration is that both are uncomfortable and impractical for use over long periods.

It is known that physostigmine is capable of passing through the blood-brain barrier to reach the nuclei where it exerts its effect. The physostigmine derivatives currently used for this purpose include salts such as those traditionally described in pharmacopeias for formulating basic alkaloids. These include the salicylate, the sulphate or the nitrate, though more lipophilic derivatives of physostigmine, such as the heptyl derivative (IT 047780) or its analogues have been developed.

Other derivatives include those described in EP-A-0 298 202. This document describes derivatives of physostigmine in which the methyl carbamate group is replaced by a $C_{2-12}$ alkyl carbamate group and claims organic salts of such derivatives with organic acids selected from tartaric, maleic and citric acids.

A further class of physostigmine derivatives are described in U.S. patent application Ser. No. 07/166,824, made publicly available by the Department of Health and Human Services through the National Technical Information Service, including (−)-N(1)-norphysostigmine, (−)-N(1)-alkylphysostigmine and (−)-N(1)-phenylethylphysostigmine.

The compounds of application Ser. No. 07/166,824 are represented by the formula

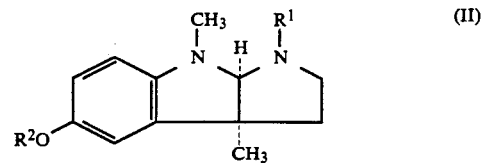

(II)

wherein
$R^1$=H, $R^2$=$CH_3$
$R^1$=Bz, $R^2$=$CH_3$
$R^1$=Bz, $R^2$=OH
$R^1$=Bz, $R^2$=OCONH—$CH_3$
$R^1$=H, $R^2$=CONH—$CH_3$
$R^1$=$CH_2$=CH—$CH_2$, $R^2$=CONH$CH_3$
$R^1$=$CH_2$—$CH_2$—Ph, $R^2$=CONH$CH_3$.

JP-0-1279830 discloses the use of physostigmine-containing compositions wherein pentaenoic and/or hexaenoic acids and phosphatidyl choline are included as excipients.

A disadvantage of the salts of physostigmine and the derivatives and compositions described hitherto is that they have an extremely short half-life and are eliminated from the blood completely within 2 hours. Physostigmine is also a highly toxic product with a small therapeutic margin, and the doses administered by conventional routes must therefore necessarily be low. We have now attempted to rationalize the use of physostigmine by devising new salts and also by administering the drug in such a way that it gains a more direct access to the brain for prolonged periods in non-toxic concentrations. In making this invention, it was surprisingly found that certain lipophilic salts of physostigmine, which are specifically the subject of the invention, when administered in an appropriate manner, can prolong the mean life of the alkaloid, so bringing significant therapeutic advantages.

DETAILED DESCRIPTION OF THE INVENTION

According to one aspect of the present invention, there are provided salts of physostigmine, or of a pharmacologically acceptable derivative thereof having anticholinesterase activity, and a phosphatidic acid.

The salts of the invention may be represented by the formula $$[PS]_x[PA]_y \qquad (III)$$

wherein
PS represents a cation derived from physostigmine, or from a pharmacologically acceptable derivative thereof having anticholinesterase activity,
PA represents a phosphatidic acid or a mixture of different phosphatidic acids, and x:y is from 2:1 to 1:2.

Preferably the ratio x:y is from 1.2:1 to 1:1.2, most preferably from 1.1:1 to 1:1.1.

In the above formula, PS is preferably physostigmine, but it can also represent a pharmacologically acceptable derivative of physostigmine, for example one of those described in IT 047780, EP 0 298 202 and U.S. Ser. No. 07/166 824.

The term "phospahatidic acid" as used herein, can represent a compound having the formula

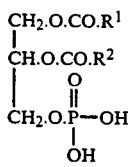

(IV)

wherein $R_1$ and $R_2$, which may be the same or different, each represents a $C_{10\text{-}24}$ alkyl group, a $C_{10\text{-}24}$ alkenyl group, or a $C_{10\text{-}24}$ alkadienyl group. Said groups respectively may be represented by the formulae $C_nH_{2n+1}$, $C_nH_{2n-1}$ or $C_nH_{2n-3}$ wherein n is from 10 to 24.

Preferably n is from 15 to 24, most preferably 15 or 17.

The salts of the invention may be prepared by a process comprising salification of (a) physostigmine, or a pharmacologically acceptable derivative thereof, with (b) one or more phosphatidic acids, each of said reactants (a) and (b) being in the free form or in the form of a salt-forming derivative. The salification is preferably carried out in a solution for both reactants. Such processes form further aspects of the invention.

The solvent is preferably selected from halogenated hydrocarbons, ketones, ethers and mixtures thereof.

The invention further provides pharmaceutical compositions comprising a salt of physostigmine, or of a pharmacologically acceptable derivative of physostigmine having anticholinesterase activity, and a phosphatidic acid, preferably one of the preferred salts defined above and a pharmaceutically acceptable excipient. The compositions are preferably provided as sustained release pharmaceutical dosage forms capable of releasing the pharmacologically active ingredient(s) over a period of time.

Such sustained release pharmaceutical dosage forms are preferably adapted to release the pharmaceutically active ingredient(s) trans-cutaneously, for example by being presented in the form of a cutaneous patch, plaster or bandage.

As indicated, the products of the present invention, namely new salts of physostigmine or of a pharmacologically acceptable derivative thereof having anticholinesterase activity, may be obtained by salification in protic or non-protic solvents of the alkaloid in the form of the base or the salt with anions of weak organic acids, with natural or synthetic phosphatidic acids, having saturated or unsaturated, homogeneous or mixed acyl chains.

The salts that can be derived from natural phosphatidic acids of vegetable origin are of particular interest. Such phosphatidic acids can be separated from common plants widely used for food such as soya, peanuts, etc. The salts may be obtained by reacting a stoichiometric quantity of the alkaloid with a stoichiometric quantity of the chosen phosphatidic acid (1M:1M).

Once formed, the salts are highly soluble in non-protic solvents and therefore exhibit pronounced lipophilia. This is believed to be due to the fact that the mobility of the lipid chains enables them to wind round the more polar nucleus of the new salts. The transcutaneous and transepidermal absorption of the salts of the invention is far superior to that of the salts used hitherto.

Given that drugs for the treatment of senile dementia must act principally in the cerebral cortex, which contains the basal ganglia that control the body's fundamental neuronal responses, it would be extremely valuable if drugs could be sent directly to the brain in a specific way without hepatic by-pass and without their having to act on other organs and body systems, thereby producing toxic effects.

It has been found that the highly lipophilic salts of alkaloids with an adrenergic or anticholinesterase action (which constitute one of the subjects of the present invention) enables this specific object to be achieved. When applied in controlled-release formulations according to the invention at the base of the neck close to the bifurcation of the branches of the internal carotid and common carotid arteries or below the ear close to the external carotid artery or the anterior auricular or posterior occipital artery, it has been found to be possible to maintain high levels of the drug in the brain for prolonged periods, as is necessary in the treatment of chronic diseases.

When the salts of phosphatidic acids with physostigmine or with a pharmacologically acceptable derivative thereof having anticholinestrase according to the invention come into contact with water they form microdispersions of a liposomal type that interact rapidly with the cell structures or diffuse freely through the tissues where they can easily reach the lumen of the arteries, whence they travel to the site of action.

The new salts can be applied to the sites described above in dosages between 0.5 and 50 mg given as one or more daily doses depending on the individual receptor response. It is clear that if consistent results are to be obtained in a chronic degenerative disease there must be a constant supply of the drug to the target organ in quantities sufficient to produce the required effect. This has been achieved using salts according to the invention.

Controlled-release transcutaneous pharmaceutical forms have proved suitable for the administration of the new salts of the invention since they enable the drug to be directed to the target organ with minimal involvement of the peripheral organs. Controlled-release plasters have proved particularly effective for this purpose since between 0.5 and 50 mg physostigmine phosphatidate can be incorporated in the reservoir. Liposomal forms of the same salt applied in the form of lipogels, with or without the presence of conventional phospholipids, have also proved effective. The plaster form has proved extremely practical for long-term use, as is necessary in treating Alzheimer's disease and other forms of senile dementia. However, the drug can also be incorporated and administered in other conventional forms such as tablets, oily solutions, suppositories, etc.

The examples set out below serve to illustrate the invention without in any way limiting its scope.

EXAMPLE I

Preparation of physostigmine dipalmitoyl glyceryl phosphatidate 2.75 g physostigmine base are dissolved in 15 ml methylene chloride with stirring, then 6.48 g dipalmitoyl glyceryl phosphatidic acid are added at ambient temperature. When the reagents have dissolved completely, the solution in methylene chloride is evaporated to dryness under vacuum at a temperature not exceeding 40° C. until the solvent has been completely eliminated. The residue is dispersed in n-hexane at 5° C. and filtered.

This yields 9.75 g of a white solid with the following characteristics: m.p. 62.2° C. $[\alpha]_D=45°$ (conc=1% in CHCl$_3$); $_{31}$P-NMR 2.23 3.15.

EXAMPLE II

Preparation of a salt of physostigmine with phosphatidic reagent 2.75 g physostigmine base are dissolved in 15 ml methylene chloride with stirring and 7 g phophatidic acid derived from hydrogenated soya and having a natural ratio of fatty acids and a mean molecular weight determined by acid-base titration of 698, are added. When the reagents have dissolved completely, the solution in methylene chloride is evaporated to dryness under vacuum at a temperature not exceeding 40° C. until the solvent has been completely eliminated. The residue is dispersed in n-hexane at 5° C. and filtered. This yields 9.75 g of a white solid with the following characteristics: m.p. 55.8° C. $[\alpha]_D=+47.7$ (conc=1% CHCl$_3$) 31$^P$-NMR 2.27 3.22.

EXAMPLE III

Preparation of plasters for transdermal absorption containing the physostigmine salt of hydrogenated soya phosphatidic acid The physostigmine salt is incorporated in an adhesive mass that controls the release of the drug and has the following composition:

| | |
|---|---|
| physosotigmine phosphatidate | 50 mg |
| lactose | 398 mg |
| saturated triglycerides | 22 mg |
| polyisobutene | 220 mg |
| hydrogenated colophony | 195 mg |
| polyalkadiene | 195 mg |

The transdermal plaster is made up of three layers, namely a backing sheet, an adhesive film containing the active principle built up by applying several coatings, and a cover sheet. The drug is released over a period of 24 h to ensure continuous administration.

I claim:

1. A salt of physostigmine and a phosphatidic acid.

2. A salt according to claim 1 having the formula $$[PS]_x[PA]_y$$

wherein PS represents a cation derived from phosostigmine, PA represents a phosphatidic acid or a mixture of different phosphatidic acids, and x:y is from 2:1 to 1:2.

3. A salt according to claim 2 wherein x:y is from 1.2:1 to 1:1.2, preferably from 1.1:1 to 1:1.1.

4. A salt according to claim 2 where PA is a phosphatidic acid having the formula

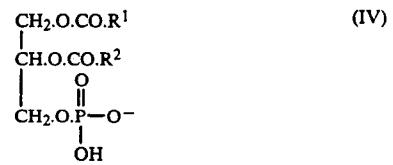

wherein R$_1$ and R$_2$, which may be the same or different, each represents a Cn alkyl group, a Cn alkenyl group, or a Cn alkadienyl group and n is an integer from 10 to 24.

5. A salt according to claim 4, wherein n is from 15 to 24.

6. A salt according to claim 5 wherein n is 15 or 17.

7. A pharmaceutical composition comprising a salt according to claim 1 and a pharmaceutically acceptable excipient.

8. A sustained release pharmaceutical dosage form capable of releasing a pharmacologically active substance over a period of time, wherein the active substance is a salt according to claim 1.

9. A sustained release pharmaceutical dosage form according to claim 8, adapted to release the pharmaceutically active substance trans-cutaneously.

10. A sustained release pharmaceutical dosage form according to claim 9 in the form of a cutaneous patch, plaster or bandage.

11. A method for treating senile dementia or Alzheimer's disease which comprises administering to a patient in need of such treatment an effective dose of a salt according to claim 1.

* * * * *